United States Patent [19]
Bandman et al.

[11] Patent Number: 5,683,910
[45] Date of Patent: Nov. 4, 1997

[54] HUMAN PHOSPHORYLASE KINASE GAMMA SUBUNIT

[75] Inventors: Olga Bandman, Mountain View; Surya K. Goli, Sunnyvale, both of Calif.

[73] Assignee: Incyte Pharmaceuticals, Inc., Palo Alto, Calif.

[21] Appl. No.: 713,828

[22] Filed: Sep. 13, 1996

[51] Int. Cl.$^6$ .............. C12N 9/14; C12N 1/20; C12N 15/00; C12P 21/06

[52] U.S. Cl. ............. 435/194; 435/193; 435/69.1; 435/252.3; 435/320.1; 530/350; 536/23.2; 424/94.5

[58] Field of Search ................. 435/69.1, 193, 435/194, 252.3, 320.1; 530/350; 424/94.5; 536/23.2

[56] References Cited

PUBLICATIONS

Bashan, N., et al., "Glycogenosis Due to Liver and Muscle Phosphorylase Kinase Deficiency" *Pediat. Res.*, 15:299–303 (1981).

Calalb, M.B., et al., "Molecular Cloning and Enzymatic Analysis of the Rat Homolog of 'PhK–γT,' an Isoform of Phosphorylase Kinase Catalytic Subunit" *J. Biol. Chem.*, 267:1455–1463 (1992).

Cawley, K.C., et al., "Nucleotide sequence of cDNA encoding the catalytic subunit of phosphorylase kinase from rat soleus muscle" *Nucleic Acids Res.*, 16:2355–2356 (1988).

Chamberlain, J.S., et al., "Isolation of cDNA clones for the catalytic γ subunit of mouse muscle phosphorylase kinase: Expression of mRNA in normal and mutant Phk mice" *Proc. Natl. Acad. Sci.*, 84:2886–2890 (1987).

Huang, C.F., et al., "Mutational Analyses of the Metal Ion and Substrate Binding Sites of Phosphorylase Kinase γ Subunit" *Biochem.*, 33:5877–5883 (1994).

Huang, C.F., et al., "Identification of the Substrate and Pseudosubstrate Binding Sites of Phosphorylase Kinase γ–Subunit" *J. Biol. Chem.*, 270:7183–7188 (1995).

Lederer, B., et al., "The Autosomal Form of Phosphorylase Kinase Deficiency in Man: Reduced Activity of the Muscle Enzyme" *Biochem. and Biophys. Res. Comm.*, 92:169–174 (1980).

Moses, S.W., "Muscle Glycogenosis" *J. Inher. Metab. Dis.*, 13:452–465 (1990).

Schneider, A., et al., "Phosphorylase kinase deficiency in I–strain mice is associated with a frameshift mutation in the α subunit muscle isoform" *Nature Genetics*, 5:381–385 (1993).

Wehner, M., et al., "Human muscle glycogenosis due to phosphorylase kinase deficiency associated with a nonsense mutation in the muscle isoform of the α subunit" *Hum. Mol. Gen.*, 3:1983–1987 (1994).

Wehner, M., et al., "Human cDNA encoding the muscle isoform of the phosphorylase kinase γ subunit (PHKG1)" *Hum Genet*, 96:616–618 (1995).

Jones et al. (1990) Biochimica et Biophysica Acta 1048:24–29, Jan. 30, 1990.

*Primary Examiner*—Robert A. Wax
*Assistant Examiner*—Tekchand Saidha
*Attorney, Agent, or Firm*—Lucy J. Billings; Incyte Pharmaceuticals, Inc.

[57] ABSTRACT

The present invention provides a novel human phosphorylase kinase gamma subunit (HPHKG) and the polynucleotide which identifies and encodes HPHKG. The invention provides for expression vectors and host cells comprising the nucleic acid sequence encoding HPHKG. The invention also provides pharmaceutical compositions containing purified HPHKG or antisense molecules to HPHKG for the treatment of diseases associated with expression of HPHKG. The invention also includes diagnostic compositions containing the polynucleotide, fragments or the complement thereof, which hybridize with the genomic sequence or the transcript of polynucleotides encoding HPHKG or anti-HPHKG antibodies which specifically bind to HPHKG, and the use of such compositions for diagnosis of disease.

6 Claims, 4 Drawing Sheets

```
                         9               18              27              36              45              54
5' MNC GGG AGC TGG GCA GGG GGA AAT TTG CAG TGG CTG ACA AAA TGT ATA AAG AAA 63              72              81              90              99             108
   GAT TCT GGG AAA GAA TTT GCT GCA AAG TTC ATG AGA AAA AGA AGA AAA GGC CAA
                                                   M   R   K   R   R   K   G   Q 117             126             135             144             153             162
   GAT TGT CGG ATG GAA ATA ATT CAT GAG ATT GCT GTA CTT GAA CTA GCA CAA GAC
   D   C   R   M   E   I   I   H   E   I   A   V   L   E   L   A   Q   D 171             180             189             198             207             216
   AAT CCT TGG GTC ATT AAT TTA CAT GAA GTT TAT GAG ACT GCA TCA GAA ATG ATC
   N   P   W   V   I   N   L   H   E   V   Y   E   T   A   S   E   M   I 225             234             243             252             261             270
   TTA GTT CTG GAA TAT GCT GCT GGG GGT GAA ATC TTT GAC CAG TGT GTT GCA AAC
   L   V   L   E   Y   A   A   G   G   E   I   F   D   Q   C   V   A   N 279             288             297             306             315             324
   AGA GAA GAT GCC TTT AAA GAA AAA GAT GTT CAA AGA CTT ATG CGA CAG ATT TTA
   R   E   D   A   F   K   E   K   D   V   Q   R   L   M   R   Q   I   L 333             342             351             360             369             378
   GAA GGT GTT CAC TTT TTA CAC ACT CGT GAT GTA GTT CAT CTT GAT TTG AAG CCT
   E   G   V   H   F   L   H   T   R   D   V   V   H   L   D   L   K   P 387             396             405             414             423             432
   CAG AAT ATT CTG TTG ACA AGT GAA TCT CCA TTG GGT GAC ATT AAG ATT GTT GAT
   Q   N   I   L   L   T   S   E   S   P   L   G   D   I   K   I   V   D 441             450             459             468             477             486
   TTT GGC CTY TCA AGA ATA TTG AAG AAC AGT GAA GAG CTC CGA GAA ATT ATG GGT
   F   G   L   S   R   I   L   K   N   S   E   E   L   R   E   I   M   G 495             504             513             522             531             540
   ACC CCT GAA TAT GTG GCT CCT GAA ATT CTT AGT TAT GAT CCT ATA AGC ATG GCA
   T   P   E   Y   V   A   P   E   I   L   S   Y   D   P   I   S   M   A 549             558             567             576             585             594
   ACA GAT ATG TGG AGC ATT GGA GTG TTA ACA TAT GTC ATG CTT ACA GGA ATA TCA
   T   D   M   W   S   I   G   V   L   T   Y   V   M   L   T   G   I   S 603             612             621             630             639             648
   CCT TTC TTA GGC AAT GAT AAA CAA GAA ACA TTC TTA AAC ATC TCA CAG ATG AAT
   P   F   L   G   N   D   K   Q   E   T   F   L   N   I   S   Q   M   N
```

FIG. 1A

```
            657           666           675           684           693           702
TTA AGT TAT TCT GAG GAA GAA TTT GAT GTT TTG TCT GAG TCG GCT GTT GAT TTC
 L   S   Y   S   E   E   E   F   D   V   L   S   E   S   A   V   D   F 711           720           729           738           747           756
ATC AGG ACA CTT TTA GTT AAG AAA CCT GAA GAT CGA GCC ACT GCT GAA GAA TGT
 I   R   T   L   L   V   K   K   P   E   D   R   A   T   A   E   E   C 765           774           783           792           801           810
CTA AAG CAC CCC TGG TTG ACA CAG AGC AGT ATT CAA GAG CCT TCT TTC AGG ATG
 L   K   H   P   W   L   T   Q   S   S   I   Q   E   P   S   F   R   M 819           828           837           846           855           864
GAA AAG GCA CTA GAA GAA GCA AAT GCC CTC CAA GAA GGT CAT TCT GTG CCT GAA
 E   K   A   L   E   E   A   N   A   L   Q   E   G   H   S   V   P   E 873           882           891           900           909           918
ATT AAT TCG GAT ACC GAC AAA TCA GAA ACC GAG GAA TCC ATT GTA ACC GAA GAG
 I   N   S   D   T   D   K   S   E   T   E   E   S   I   V   T   E   E 927           936           945           954           963           972
TTA ATT GTA GTT ACT TCA TAT ACT CTA GGA CAA TGC AGA CAG TCT GAA AAA GAG
 L   I   V   V   T   S   Y   T   L   G   Q   C   R   Q   S   E   K   E 981           990           999          1008          1017          1026
AAA ATG GAG CAA AAG GCC ATT TCC CAA ACG ATT TAA ATT TGA GGA ACC TTT GCC
 K   M   E   Q   K   A   I   S   Q   T   I 1035          1044          1053          1062          1071          1080
TAC AAG AAA TTC CAG GAG AAT TTA TCT ACT GAG CAA TAT TTC CCT TTA GAA CTT 1089          1098          1107          1116          1125          1134
CAA GAT TTC TAC ACT GAA AAT GTT AAT ATT ATT TAT GGA CCT CTG GCC AAA TGG 1143          1152          1161          1170          1179          1188
TAC ATG TAC TGG AAG TGG ATA ACC AGT ATC ACT TAC ACA AAC AAA AAT AAC TTT 1197          1206          1215          1224          1233          1242
GTC AAA TTT GTG GAG TTA GGT GGA AGC CAG ATT TTA AAA GTT GCC AAC CAG GAT 1251          1260          1269          1278          1287          1296
ATT TAA CAG GTA CAG TTA CCC GTT TCA ATG TTA TTT TTA AGA AGG GAG ATG TTG 1305          1314          1323          1332          1341          1350
GCA CCT TTG AAT TCT ACA TCC TGT TTC TCC AGA ATG AGA ATT TGT GTA CAA AGA 1359          1368          1377          1386          1395          1404
TAT TTG TAT TCA CTT TCT TTA AAA AAT CCA AGT AAA AGT GCC AAA ACT ACA AAA

1413
AAA AAA AAA AAA AAA  3'
```

```
238 PS-------FRMEKALEEANALQEGHSVPE          56494
296 VRHFSPRGKFKVI-ALTVLASVRIYYQYRR          g1147567
296 VRHFSPRGKFKVI-CLTVLASVRIYYQYRR          g56927
296 VRHFSPRGKFKVI-CLTVVASVKIYYQYRR          g200341

261 INSDTDKSETEESIVTEELI-VVTSYTLGQ          56494
325 VKPVTREIVIRDPYALRPLRRLIDAYAFRI          g1147567
325 VKPVTREIVIRDPYALRPLRRLIDAYAFRI          g56927
325 VKPVTREIVIRDPYALRPLRRLIDAYAFRI          g200341

290 CRQSEKEKMEQ-----------KAI------          56494
355 YGHWVKKGQQQNRAALFENTPKAVLLSLAE          g1147567
355 YGHWVKKGQQQNRAALFENTPKAVLLSLAE          g56927
355 YGHWVKKGQQQNRAALFENTPKAVLLSLAE          g200341

304 SQTI                                    56494
385 E-DY                                    g1147567
385 EEDF                                    g56927
385 EEDF                                    g200341
```

HUMAN PHOSPHORYLASE KINASE GAMMA SUBUNIT

FIELD OF THE INVENTION

The present invention relates to nucleic acid and amino acid sequences of a novel human phosphorylase kinase gamma subunit and to the use of these sequences in the diagnosis, study, prevention and treatment of disease.

BACKGROUND OF THE INVENTION

The biopolymer glycogen is the major storage form of glucose as an energy source in the body. Regulation of the enzyme, glycogen phosphorylase (GP), modulates the catabolic breakdown of glycogen in various tissues and in distinct stages of cell development by mobilizing glucose reserves for ATP energy production. GP is under a complex set of controls that prevent glycogen breakdown except when ATP is needed. The breakdown of glycogen involves substrates, intermediates, cofactors, activators, inhibitors, enzymatic interconversions and hormonal interactions. When blood glucose is low, GP is activated and causes muscle and liver glycogen to be broken down to yield glucose. The rate of glucose mobilization by this system is regulated by a cascade of kinase reactions initiated by epinephrine and an increase of calcium ions in the cytosol. Glucose produced from glycogen in muscle cells is oxidized quickly to $CO_2$ yielding ATP as a source of energy for muscle contraction. Glucose generated from liver glycogen is secreted into the blood where it serves as an energy source for many body tissues that do not store energy reserves, such as the brain.

Glycogen phosphorylase exists in active (phosphorylase a) and inactive (phosphorylase b) forms, the ratio of which is controlled by the rate of interconversion between the different forms and affects the rate of conversion of glycogen into glucose. Activation occurs through the phosphorylation of GP at specific serine residues by the enzyme, phosphorylase kinase (Phk), a $Ca^{2+}$ dependent enzyme. The activity of GP (hence the catabolic breakdown of glycogen) therefore depends upon its phosphorylation by Phk.

Glycogen phosphorylase, and its activation through phosphorylase kinase (Phk), is situated at a strategically important point between the fuel reservoir, glycogen, and the glycolytic pathways that provide glucose as fuel for various cellular activities underlying tissue maintenance and development. Heritable deficiencies in Phk underlie a remarkably heterogeneous group of glycogen utilization disorders in humans. At least ten different forms of Phk deficiency have been described (Schneider A et al (1993) Nature Gene 5:381–385)

Phk is one of the largest and most complex of the known protein kinases. The enzyme has a quaternary structure based upon 4 subunits: alpha, beta, gamma, and delta. Phosphorylase kinase exists in an active phosphorylated form and an inactive dephosphorylated form. The regulatory alpha and beta subunits are phosphorylated by cAMP-dependent protein kinase. The delta subunit is calmodulin and mediates regulation by $Ca^{2+}$. The binding of $Ca^{2+}$ to the delta subunit activates the complex, which is maximally active if at least the alpha subunit is phosphorylated. The N-terminal region of the gamma subunit contains the catalytic protein kinase domain, within approximately residues 1–300, while the C-terminal region (approximately residues 300–385) contains two of the important calmodulin-binding domains required to activate the protein complex (Huang CY, et al (1995) J Biol Chem 270(13):7183–7188). Within this subunit, residues Glu(E) 111 and Glu(E) 154 are purported to be important for substrate binding (Huang et al, supra) and residues Asn(N) 155, Asp(D) 168, Phe(F) 169, and Gly(G) 170 are important for catalytic activity (Huang CY et al (1994)Biochem 33 (19:5877–83). Mutations affecting different subunits, especially the catalytic gamma subunit, are expected to contribute to genetic heterogeneity (Wehner M et al (1994) Hum Mol Genet 3 (11):1983–87). Two isoforms, each encoded by separate genes, are currently known for the gamma subunit in muscle and testis (Calalb MB et al (1992) J Biol Chem 267:1455–63).

Phosphorylase kinase deficiency has significant potential for genetic heterogeneity, since the enzyme is composed of four non-identical subunits. Inborn genetic errors affecting glycogen breakdown, namely deficiencies of phosphorylase kinase (Phk), have been reviewed (Moses SW (1990) J Inherit Metab Dis 13 (4):452–65). Moreover, deficiency of glycogen catabolic functions have been frequently reported in families as well as in reports of different enzyme defects among siblings. Mutations affecting different subunits and isoforms of Phk are expected to contribute to this genetic heterogeneity (Wehner M et al, supra).

Muscle glycogenosis caused by Phk deficiency leads to exercise intolerance, weakness and muscular atrophy. Hepatic Phk deficiency is also associated with certain hepatic diseases characterized by hypoglycemia and hepatomegaly. Severe muscular (myopathic) forms of Phk deficiency have been reported which start in infancy, as well as a late onset form, and are characterized by exercise intolerance and muscle cramps. Another autosomal recessively inherited variant in which both liver and muscle enzymes were affected has been described separately in two families (Lederer B et al (1980) Biochem Biophys Res Commun 92:169–174; Bashan N et al (1981)Pediatr Res 15:299) Experts have frequently suggested that genes which are responsible for these conditions, as well as ones for enzyme replacement therapy, should be sought (Wehner M et al (1995) Hum Genet 96(5):616–618 ).

No primary therapy for the Phk enzyme deficiency is presently available in any of the glycogenoses. The main therapeutic efforts are dietary in nature. Patients with enzyme deficiencies have in their early years limited fasting tolerances. These characteristics of hypoglycemia are addressed with frequent feedings, nocturnal gastric infusions of glucose and uncooked cornstarches. High protein diets have also been advocated but have not been shown to prevent the course of disease, especially in infantile forms. Most infantile cases are lethal within two years (Moses SW (1990) J Inherit Metab Dis 13 (4):452–65).

It is therefore clear that there continues to be a significant longfelt need for agents which are useful for the detection, treatment, and correction of pathophysiological conditions caused by aberrant forms of the PHK and by deficiencies in PHK activity.

SUMMARY OF THE INVENTION

The present invention discloses a novel human phosphorylase kinase gamma subunit (HPHKG) characterized as having homology to other phosphorylase kinase gamma subunits. Accordingly, the invention features substantially purified HPHKG, having the amino acid sequence of SEQ ID NO:1 and which have characteristics of other phosphorylase kinase gamma members.

One aspect of the invention features an isolated and substantially purified polynucleotide which encodes HPHKG. In a particular aspect, the polynucleotide is the nucleotide sequence of SEQ ID NO:2. In addition, the invention features polynucleotide sequences that hybridize under stringent conditions to SEQ ID NO:2.

The present invention also relates to an expression vector which includes a polynucleotide encoding an HPHKG and its use to transform host cells or organisms.

The present invention also relates to methods for making HPHKG, anti-HPHKG antibodies and pharmaceutical compositions comprising HPHKG or nucleic acids encoding HPHKG.

BRIEF DESCRIPTION OF THE FIGURES

FIG. 1A and 1B shows the nucleic acid sequence (SEQ ID NO:2) and amino acid sequence (SEQ ID NO:1) of the human phosphorylase kinase gamma subunit, HPHKG. The alignment was produced using MacDNAsis software (Hitachi Software Engineering Co Ltd, San Bruno, Calif.).

FIG. 2A and 2B shows the amino acid sequence alignments between HPHKG, and the phosphorylase kinase gamma from human muscle (GI 1147567; SEQ ID NO:3), mouse muscle (GI 200341; SEQ ID NO:4), and rat muscle (GI 56927; SEQ ID NO:5). The alignments were produced using the multisequence alignment program of DNAStar software (DNAStar Inc, Madison, Wis.).

DETAILED DESCRIPTION OF THE INVENTION

Definitions

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to protein or peptide sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

As used herein, "HPHKG" refers to the amino acid sequence of substantially purified HPHKG from any source whether natural, synthetic, semi-synthetic or recombinant.

A "variant" of HPHKG is defined as an amino acid sequence that is different by one or more amino acid substitutions. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HPHKG.

A "substitution" results from the replacement of one or more nucleotides or amino acids by different nucleotides or amino acids, respectively.

The term "biologically active" refers to a HPHKG having structural, regulatory or biochemical functions of the naturally occurring HPHKG. Likewise, "immunologically active" defines the capability of the natural, recombinant or synthetic HPHKG, or any oligopeptide thereof, to induce a specific immune response in appropriate animals or cells and to bind with specific antibodies.

The term "derivative" as used herein refers to the chemical modification of a nucleic acid sequence encoding HPHKG or the encoded HPHKG. Illustrative of such modifications would be replacement of hydrogen by an alkyl, acyl, or amino group. A nucleic acid derivative would encode a polypeptide which retains essential biological characteristics of natural HPHKG.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York, N.Y.). Amplification as carried out in the polymerase chain reaction technologies is described in Dieffenbach CW and GS Dveksler (1995, PCR Primer, a *Laboratory Manual*, Cold Spring Harbor Press, Plainview, N.Y.).

Preferred Embodiment

The present invention relates to a novel human phosphorylase gamma subunit, HPHKG, initially identified among the partial cDNAs from a WI38 lung fibroblast cell line library (FIBRNOT01) and to the use of the nucleic acid and amino acid sequences disclosed herein in the study, diagnosis, prevention and treatment of disease.

In addition to the above mentioned source, northern analysis indicates that nucleic acid sequence encoding a portion of HPHKG was also found in cDNA libraries from pancreatic tissue and placenta.

The present invention also encompasses HPHKG variants. A preferred HPHKG variant is one having at least 80% amino acid sequence similarity to the HPHKG amino acid sequence (SEQ ID NO:1), a more preferred HPHKG variant is one having at least 90% amino acid sequence similarity to SEQ ID NO:1, and a most preferred HPHKG variant is one having at least 95% amino acid sequence similarity to SEQ ID NO:1.

Nucleic acid encoding a portion of HPHKG was first identified in the cDNA, Incyte Clone 56494, through a computer-generated search for amino acid sequence alignments. The nucleic acid sequence, SEQ ID NO:2, disclosed herein encodes the amino acid sequences, SEQ ID NO:1. The present invention is based, in part, on the chemical and structural homology among HPHKG and various known phosphorylase kinase gamma, and to various amino acid sequence motifs within these proteins that are characteristic of the catalytic domain of phosphorylase kinase gamma (Hardie G and Hanks S (1995), *The Protein Kinase Facts Books*, I and II, Academic Press, San Diego, Calif.).

Figure 2A:
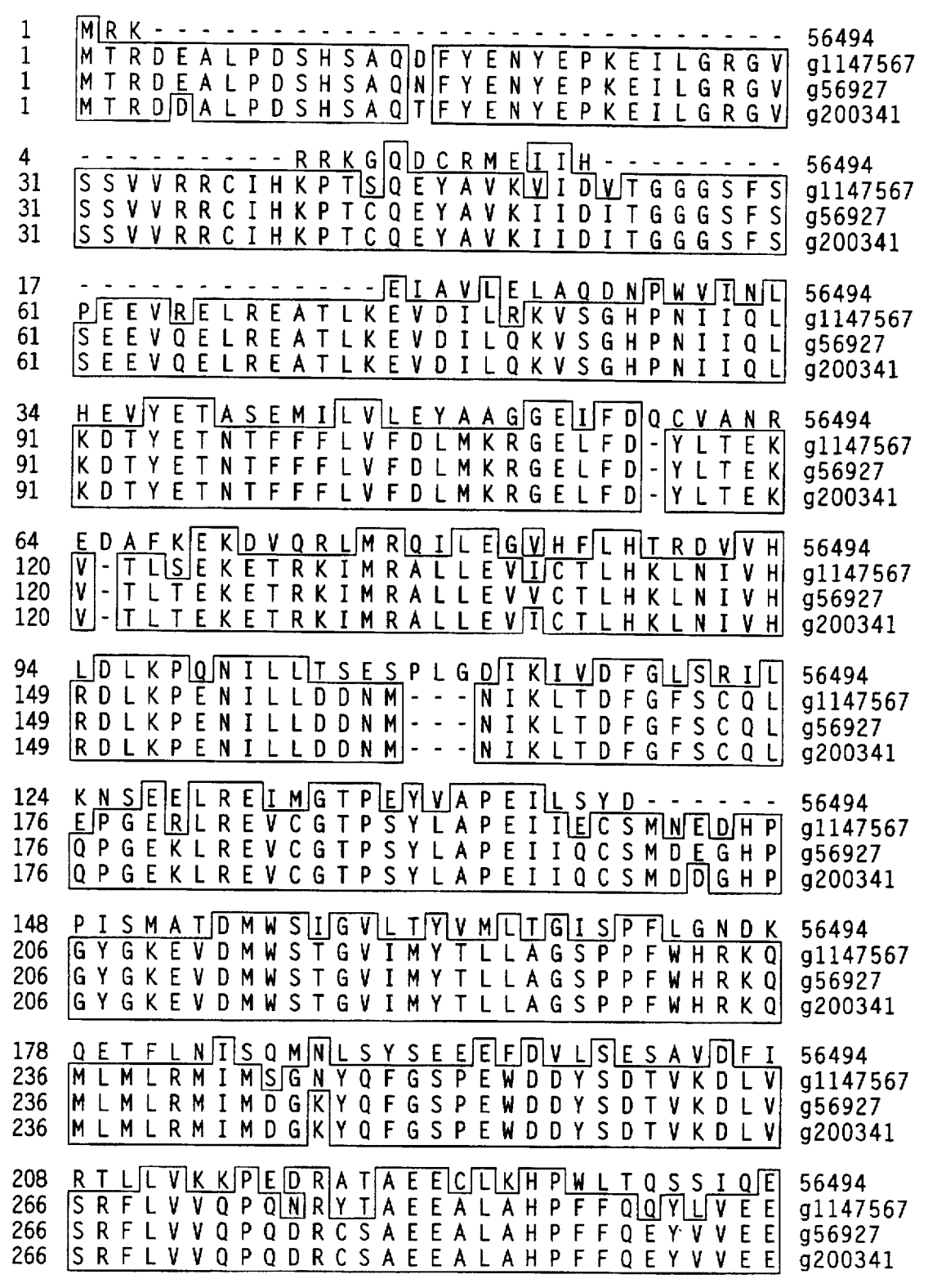

Referring to FIG. 2, the similarities in amino acid sequences among HPHKG and phosphorylase kinase gamma from various sources are evident. This comparison illustrates that the most conserved domains of the phosphorylase kinase gamma are clustered around the active sites of the molecule and, in particular, are in the region of the molecule corresponding to the catalytic domain between residues 1–300 (Huang et al, supra). The substrate binding site of the human phosphorylase kinase gamma muscle isoform (GI 1147567; SEQ ID NO:3), at Glu(E) 111, which corresponds to Glu(E) 54 of HPHKG (SEQ ID NO:2), is conserved as well as 8 residues (DLKP and NILL) on both sides of Glu(E) 154, corresponding to residue 99 of SEQ ID NO:2. Furthermore, the important catalytic sites of SEQ ID NO:3 at residues Asn(N) 155, Asp(D) 168, Phe(F) 169, and Gly(G) 170 are also conserved in the novel HPHKG. These same sequences are further conserved in both the mouse (GI 200341; SEQ ID NO:4), and rat (GI 56927; SEQ ID NO:5) phosphorylase kinase gamma. Additional regions of sequence identity between HPHKG and the other phosphorylase kinase gamma are found within the catalytic domain beginning at residue 134 for HPHKG (GTP-Y-APEI), at residue 154 (DMWS-GV) and at residue 221 (TAEE-L-HP).

The HPHKG Coding Sequences

The nucleic acid and deduced amino acid sequences of HPHKG are shown in FIG. 1. In accordance with the invention, any nucleic acid sequence which encodes the amino acid sequence of HPHKG can be used to generate recombinant molecules which express HPHKG. In a specific embodiment described herein, a partial sequence of HPHKG was first isolated as Incyte Clone 56494 from a WI38 lung fibroblast cell line cDNA library (FIBRNOTO1)

It will be appreciated by those skilled in the art that as a result of the degeneracy of the genetic code, a multitude of HPHKG-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring HPHKG, and all such variations are to be considered as being specifically disclosed.

Although nucleotide sequences which encode HPHKG and its variants are preferably capable of hybridizing to the nucleotide sequence of the naturally occurring HPHKG under appropriately selected conditions of stringency, it may be advantageous to produce nucleotide sequences encoding HPHKG or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HPHKG and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a HPHKG and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a HPHKG sequence or any portion thereof.

Also included within the scope of the present invention are polynucleotide sequences that are capable of hybridizing to the nucleotide sequence of FIG. 1 under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined stringency.

Altered nucleic acid sequences encoding HPHKG which may be used in accordance with the invention include deletions, insertions or substitutions of different nucleotides resulting in a polynucleotide that encodes the same or a functionally equivalent HPHKG. The protein may also show deletions, insertions or substitutions of amino acid residues which produce a silent change and result in a functionally equivalent HPHKG. Deliberate amino acid substitutions may be made on the basis of similarity in polarity, charge, solubility, hydrophobicity, hydrophilicity, and/or the amphipathic nature of the residues as long as the biological activity of HPHKG is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of hphkg. As used herein, an "allele" or "allelic sequence" is an alternative form of hphkg. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland, Ohio)), Taq polymerase (Perkin Elmer, Norwalk, Conn.), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

Extending the Polynucleotide Sequence

The polynucleotide sequence encoding HPHKG may be extended utilizing partial nucleotide sequence and various methods known in the art to detect upstream sequences such as promoters and regulatory elements. Gobinda et al (1993; PCR Methods Applic. 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker JD et al (1991; Nucleic Acids Res 19:3055–60). Additionally, one can use PCR, nested primers and PromoterFinder libraries to walk in genomic DNA (PromoterFinder™ Clontech, Palo Alto, Calif.). This process avoids the need to screen libraries and is useful in finding intron/exon junctions. Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' non-translated regulatory region.

Capillary electrophoresis may be used to analyze the size or confirm the nucleotide sequence of sequencing or PCR products. Systems for rapid sequencing are available from Perkin Elmer, Beckman Instruments (Fullerton, Calif.), and other companies. Capillary sequencing may employ flowable polymers for electrophoretic separation, four different fluorescent dyes (one for each nucleotide) which are laser activated, and detection of the emitted wavelengths by a charge coupled devise camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Expression of the Nucleotide Sequence

In accordance with the present invention, polynucleotide sequences which encode HPHKG, fragments of the polypeptide, fusion proteins or functional equivalents thereof may be used in recombinant DNA molecules that direct the expression of HPHKG in appropriate host cells. Due to the inherent degeneracy of the genetic code, other DNA sequences which encode substantially the same or a functionally equivalent amino acid sequence, may be used to clone and express HPHKG. As will be understood by those of skill in the art, it may be advantageous to produce HPHKG-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of hphkg expression or to produce recombinant RNA transcripts having desirable properties, such as a longer half-life, than transcripts produced from naturally occurring sequence.

The nucleotide sequences of the present invention can be engineered in order to alter a hphkg coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant sequence encoding HPHKG may be ligated to a heterologous sequence to encode a fusion protein. For example, for screening of peptide libraries for inhibitors of HPHKG activity, it may be useful to encode a chimeric HPHKG protein that is recognized by a commercially available antibody. A fusion protein may also be engineered to contain a cleavage site located between a HPHKG sequence and the heterologous protein sequence, so that the HPHKG may be cleaved and substantially purified away from the heterologous moiety.

In an alternate embodiment of the invention, the coding sequence of hphkg may be synthesized, whole or in part, using chemical methods well known in the art (see Caruthers MH et al (1980) Nuc Acids Res Symp Ser 215–23, Horn T et al (1980) Nuc Acids Res Symp Ser 225–32, etc). Alternatively, the protein itself could be produced using chemical methods to synthesize a HPHKG amino acid sequence, whole or in part. For example, peptide synthesis can be performed using various solid-phase techniques (Roberge JY et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg. Creighton (1983) *Proteins, Structures and Molecular Principles*, WH Freeman and Co, New York, N.Y.). The composition of the synthetic peptides may be confirmed by amino acid analysis or sequencing (eg, the Edman degradation procedure; Creighton, supra). Additionally the amino acid sequence of HPHKG, or any part thereof, may be altered during direct synthesis and/or combined using chemical methods with sequences from other proteins, or any part thereof, to produce a variant polypeptide.

Expression Systems

In order to express a biologically active HPHKG, the nucleotide sequence encoding HPHKG or its functional equivalent, is inserted into an appropriate expression vector, ie, a vector which contains the necessary elements for the transcription and translation of the inserted coding sequence.

Methods which are well known to those skilled in the art can be used to construct expression vectors containing a HPHKG coding sequence and appropriate transcriptional or translational controls. These methods include in vitro recombinant DNA techniques, synthetic techniques and in vivo recombination or genetic recombination. Such techniques are described in Sambrook et al (1989) *Molecular*

*Cloning, A Laboratory Manual*, Cold Spring Harbor Press, Plainview, N.Y. and Ausubel FM et al (1989) *Current Protocols in Molecular Biology*, John Wiley & Sons, New York, N.Y.

A variety of expression vector/host systems may be utilized to contain and express a HPHKG coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg. baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of hphkg, vectors based on SV40 or EBV may be used with an appropriate selectable marker.

In bacterial systems, a number of expression vectors may be selected depending upon the use intended for HPHKG. For example, when large quantities of HPHKG are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the hphkg coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HPHKG may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry LE in McGraw Hill *Yearbook of Science and Technology* (1992) McGraw Hill New York, N.Y., pp 191–196 or Weissbach and Weissbach (1988) *Methods for Plant Molecular Biology*, Academic Press, New York, N.Y., pp 421–463.

An alternative expression system which could be used to express hphkg is an insect system. In one such system, *Autographa californica* nuclear polyhedrosis virus (AcNPV) is used as a vector to express foreign genes in *Spodoptera frugiperda* cells or in Trichoplusia larvae. The hphkg coding sequence may be cloned into a nonessential region of the virus, such as the polyhedrin gene, and placed under control of the polyhedrin promoter. Successful insertion of hphkg will render the polyhedrin gene inactive and produce recombinant virus lacking coat protein coat. The recombinant viruses are then used to infect *S. frugiperda* cells or Trichoplusia larvae in which HPHKG is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a hphkg coding sequence may be ligated into an adenovirus transcription/translation complex consisting of the late promoter and tripartite leader sequence. Insertion in a nonessential E1 or E3 region of the viral genome will result in a viable virus capable of expressing HPHKG in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a hphkg sequence. These signals include the ATG initiation codon and adjacent sequences. In cases where hphkg, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express hphkg may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes CA et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the hphkg is inserted within a marker gene sequence, recombinant cells containing hphkg can be identified by the absence of marker gene function. Alternatively, a marker gene can be placed in tandem with a HPHKG sequence under the control of a single promoter. Expression of the marker gene in response to induction or selection usually indicates expression of the tandem hphkg as well.

Alternatively, host cells which contain the coding sequence for hphkg and express HPHKG may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding HPHKG can be detected by DNA-DNA or DNA-RNA hybridization or amplification using probes, portions or fragments of hphkg. Nucleic acid amplification based assays involve the use of oligonucleotides or oligomers based on the sequence encoding HPHKG to detect transformants containing hphkg DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HPHKG, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HPHKG is preferred, but a competitive binding assay may be employed. These and other assays are described, among other places, in Hampton R et al (1990, *Serological Methods, a Laboratory Manual*, APS Press, St Paul, Minn.) and Maddox DE et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to hphkg include oligolabeling, nick translation, end-labeling or PCR amplification using a labeled nucleotide. Alternatively, the hphkg sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of HPHKG

Host cells transformed with a nucleotide sequence encoding HPHKG may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding HPHKG can be designed with signal sequences which direct secretion of HPHKG through a prokaryotic or eukaryotic cell membrane. Other recombinant constructions may join hphkg to nucleotide sequence encoding a polypeptide domain which will facilitate purification of soluble proteins (Kroll DJ et al (1993) DNA Cell Biol 12:441–53).

HPHKG may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle, Wash.). The inclusion of a clearable linker sequences such as Factor XA or enterokinase (Invitrogen, San Diego, Calif.) between the purification domain and HPHKG is useful to facilitate purification. One such expression vector provides for expression of a fusion protein comprompising an HPHKG and contains nucleic acid encoding 6 histidine residues followed by thioredoxin and an enterokinase cleavage site. The histidine residues facilitate purification on IMIAC (immobilized metal ion affinity chromotography as described in Porath et al (1992) Protein Expression and Purification 3:263–281) while the enterokinase cleavage site provides a means for purifying the neuronatin from the fusion protein.

In addition to recombinant production, fragments of HPHKG may be produced by direct peptide synthesis using solid-phase techniques (cf Stewart et al (1969) Solid-Phase Peptide Synthesis, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. Various fragments of HPHKG may be chemically synthesized separately and combined using chemical methods to produce the full length molecule.

Uses of HPHKG

The rationale for the use of nucleotide and polypeptide sequences disclosed herein is based in part on the chemical and structural homology among the novel HPHKG and known phosphorylase kinase gamma from human (GI 1147567; SEQ ID NO:3, mouse (GI 200341; SEQ ID NO:4), and rat (GI 56927; SEQ ID NO:5). Decreased expression of HPHKG due to mutation or deficient expression of the gene encoding HPHKG may contribute to various pathophysiological conditions associated with diminished glycogen utilization and consequent glucose depletion. Such conditions would include muscle glycogenosis, involving muscular weakness and atrophy, and hypoglycemia, which may lead to various metabolic abnormalities including poor growth and kidney dysfunction or failure.

Increasing HPHKG activity to normal levels by administration of pharmaceutical compositions containing HPHKG, by gene therapy using sequences to express HPHKG, or by the use of agonists administered to increase the activity of endogenous HPHKG, all may be used to reverse conditions of diminished glucose production due to decreased HPHKG activity. Alternatively, antisense molecules may be directed against mutated forms of the gene that expresses dysfunctional HPHKG and may compete with normal HPHKG in the course or providing necessary levels of phosphorylase kinase activity.

HPHKG and/or a cell line that expresses HPHKG may be used to evaluate, screen and identify compounds, synthetic drugs, antibodies, peptides or other molecules that modulate the activity of HPHKG and may therefore be useful in the treatment of disease conditions associated with expression of HPHKG.

HPHKG Antibodies

HPHKG-specific antibodies are useful for the diagnosis of conditions and diseases associated with expression of HPHKG. Such antibodies may include, but are not limited to, polyclonal, monoclonal, chimeric, single chain, Fab fragments and fragments produced by a Fab expression library. Neutralizing antibodies, ie. those which inhibit dimer formation, are especially preferred for diagnostics and therapeutics.

HPHKG for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably they should mimic a portion of the amino acid sequence of the natural protein and may contain the entire amino acid sequence of a small, naturally occurring molecule. Short stretches of HPHKG amino acids may be fused with those of another protein such as keyhole limpet hemocyanin and antibody produced against the chimeric molecule. Procedures well known in the art can be used for the production of antibodies to HPHKG.

For the production of antibodies, various hosts including goats, rabbits, rats, mice, etc may be immunized by injection with HPHKG or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and Corynebacterium parvum are potentially useful human adjuvants.

Monoclonal antibodies to HPHKG may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, New York, N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HPHKG-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86:3833–3837), and Winter G and Milstein C (1991; Nature 349:293–299).

Antibody fragments which contain specific binding sites for HPHKG may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse WD et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HPHKG and its specific antibody and the measurement of complex formation. A two-site, monoclonal-based immunoassay utilizing monoclonal antibodies reactive to two noninterfering epitopes on a specific HPHKG protein is preferred, but a competitive binding assay may also be employed. These assays are described in Maddox DE et al (1983, J Exp Med 158:1211).

Diagnostic Assays Using HPHKG Specific Antibodies

Particular HPHKG antibodies are useful for the diagnosis of conditions or diseases characterized by expression of HPHKG or in assays to monitor patients being treated with HPHKG, agonists or inhibitors. Diagnostic assays for HPHKG include methods utilizing the antibody and a label to detect HPHKG in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HPHKG, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HPHKG is preferred, but a competitive binding assay may be employed. These assays are described, among other places, in Maddox, DE et al (1983, J Exp Med 158:1211).

In order to provide a basis for diagnosis, normal or standard values for HPHKG expression must be established. This is accomplished by combining body fluids or cell extracts taken from normal subjects, either animal or human, with antibody to HPHKG under conditions suitable for complex formation which are well known in the art. The amount of standard complex formation may be quantified by comparing various artificial membranes containing known quantities of HPHKG with both control and disease samples from biopsied tissues. Then, standard values obtained from normal samples may be compared with values obtained from samples from subjects potentially affected by disease. Deviation between standard and subject values establishes the presence of disease state.

Drug Screening

HPHKG, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HPHKG and the agent being tested, may be measured.

Another technique for drug screening which may be used provides for high throughput screening of compounds having suitable binding affinity to the HPHKG is described in detail in Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HPHKG and washed. Bound HPHKG is then detected by methods well known in the art. Substantially purified HPHKG can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HPHKG specifically compete with a test compound for binding HPHKG. In this manner, the antibodies can be used to detect the presence of any peptide which shares one or more antigenic determinants with HPHKG.

Uses of the Polynucleotide Encoding HPHKG

A polynucleotide expressing HPHKG, or any part thereof, may be used for diagnostic and/or therapeutic purposes. For diagnostic purposes, the sequence of this invention, or its complement, may be used to detect and quantitate gene expression in biopsied tissues in which expression may be implicated. The diagnostic assay is useful to distinguish between absence, presence, and excess expression of the sequence and to monitor regulation of sequence levels during therapeutic intervention. The association of HPHKG with disorders and disease conditions in specific tissues would greatly facilitate studies aimed at determining HPHKG function in these conditions and the development of therapeutic strategies to treat them. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding HPHKG or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring hphkg, alleles or related sequences.

Probes may also be used for the detection of related sequences and should preferably contain at least 50% of the nucleotides from any of these HPHKG encoding sequences. The hybridization probes of the subject invention may be derived from the nucleotide sequences of SEQ ID Nos:2, 4, and 6 or from genomic sequences including promoter, enhancer elements and introns of the naturally occurring hphkg. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding HPHKG include the cloning of nucleic acid sequences encoding HPHKG or HPHKG derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding HPHKG may be used for the diagnosis of conditions or diseases with which the expression of HPHKG is associated. For example, polynucleotide sequences encoding HPHKG may be used in hybridization or PCR assays of fluids or tissues from biopsies to detect hphkg expression. The form of such qualitative or quantitative methods may include southern or northern analysis, dot blot or other membrane-based technologies; PCR technologies; dip stick, pin, chip and ELISA technologies. All of these techniques are well known in the art and are the basis of many commercially available diagnostic kits.

The nucleotide sequences encoding HPHKG disclosed herein provide the basis for assays that detect activation or induction of hphkg associated with specific diseases. The HPHKG encoding nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of hphkg nucleotide sequences in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for hphkg expression must be established. This is accomplished by combining body fluids or cell extracts taken from normal subjects, either animal or human, with HPHKG encoding nucleotides, or a portion thereof, under conditions suitable for hybridization or amplification. Standard hybridization may be quantified by comparing the values obtained for normal subjects with a dilution series of an HPHKG encoding nucleotide sequence run in the same experiment where a known amount of substantially purified HPHKG encoding sequence is used. Standard values obtained from normal samples may be compared with values obtained from samples from patients afflicted with HPHKG-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the HPHKG sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby PC et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

For therapeutic purposes, an antisense molecule of an HPHKG encoding sequence may provide a basis for treatment where down-regulation of the gene and consequent inhibition of its activity is desirable. Alternatively, sequences encoding HPHKG itself may provide the basis for gene therapy in conditions where it may be desirable to increase expression of HPHKG and hence increase its activity. Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense molecules to HPHKG encoding nucleotide sequences. See, for example, the techniques described in Sambrook et al (supra) and Ausubel et al (supra).

The polynucleotides comprising full length cDNA sequence and/or its regulatory elements enable researchers to use HPHKG encoding sequences as an investigative tool in sense (Youssoufian H and HF Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding HPHKG can be turned off by transfecting a cell or tissue with expression vectors which express high levels of a desired HPHKG encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of HPHKG encoding sequences, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al (In: Huber BE and BI Carr (1994) *Molecular and Immunologic Approaches*, Futura Publishing Co, Mt Kisco, N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of hphkg.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HPHKG. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for hphkg disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for HPHKG can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York, N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a hphkg on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, a sequence tagged site based map of the human genome was recently published by the Whitehead-MIT Center for Genomic Research (Hudson TJ et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HPHKG, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that molecules or compounds that modulate HPHKG activity, such as antibodies of HPHKG, or an HPHKG derivative can be delivered in a suitable formulation as a therapeutic agent. Similarly, administration of agonists should also improve the activity or lifespan of this protein.

The examples below are provided to illustrate the subject invention and are not included for the purpose of limiting the invention.

EXAMPLES cDNA Library Construction

The AFCW cell line is a normal, homogeneous, well characterized early passage fibroblast cell culture of fibroblasts cell line WI-38 (ATCC No. CCC75, Rockville, Md.). A batch of 1×108 fibroblast cells was harvested for the library.

The fibroblast cell (AFCW) cDNA library was custom constructed by Stratagene (catalogue #937207, Stratagene, La Jolla, Calif.). Poly(A+) RNA (mRNA) was purified from the AFCW cells, and cDNA synthesis was primed with oligo d(T) primers. The AFCW cDNA library was constructed using the Lambda gt11 vector system following the procedure of Young and Davis, or Jendrisak et al, both incorporated by reference ((1983) Proc Natl Acad Sci USA 80: 1194; (1987, *Guide to Molecular Cloning Techniques*, ed Berger SL and Kimmel AR pp.359-371).

The AFCW cDNA libraries can be screened with either DNA probes or antibody probes. The custom-constructed library phage particles were infected into *E. coli* host strain XL1-Blue® (Stratagene), which has a high transformation efficiency, increasing the probability of obtaining rare, under-represented clones in the cDNA library.

II Isolation and Sequencing of cDNA Clones

The cDNA inserts from random isolates of the lambda phage library were excised and cloned into suitable phagemid vectors. The techniques for excising inserts and cloning into suitable phagemid vectors are well known in the art. Additionally, phagemid vectors having origins of replication for single-stranded-DNA-phages, and sequences suitable for expressing polypeptides from the cDNA, are also well known in the art.

The cDNA inserts from isolates of the AFCW phagemid libraries were sequenced in part. Methods for DNA sequencing are well known in the art. Conventional enzymatic methods employ DNA polymerase Klenow fragment, SequenaseTM or Taq polymerase to extend DNA chains from an oligonucleotide primer annealed to the DNA template of interest. Methods have been developed for the use of both single- and double-stranded templates. The chain termination reaction products are usually electrophoresed on urea-acrylamide gels and are detected either by autoradiography (for radionuclide-labelled precursors) or by fluorescence (for fluorescent-labelled precursors). Recent improvements in mechanized reaction preparation, sequencing and analysis using the fluorescent detection method (such as the Applied Biosystems 373 DNA sequencer and Catalyst 800).

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290-300; Altschul, SF et al (1990) J Mol Biol 215:403-10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al supra). Analogous computer techniques using BLAST (Altschul SF 1993 and 1990, supra) are used to search for identical or related molecules in nucleotide databases such as GenBank or the LIFESEQ™ database (Incyte, Palo Alto, Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search are presented as a list of libraries in which the full length sequence, or parts thereof, is represented, the abundance of the sequence, and the percent abundance. Abundance directly reflects the number of times a particular transcript is present in a cDNA library, and percent abundance is abundance divided by the total number of sequences examined in the library.

V Extension of HPHKG to Full Length or to Recover Regulatory Elements

The nucleic acid sequence encoding HPHKG (SEQ ID No:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF).

Primers allow the extension of the known HPHKG encoding sequence "outward" generating amplicons containing new, unknown nucleotide sequences for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown, Mass.) and the following parameters:

| Step 1 | 94% C for 1 min (initial denaturation) |
| Step 2 | 65% C for 1 min |
| Step 3 | 68% C for 6 min |
| Step 4 | 94% C for 15 sec |
| Step 5 | 65% C for 1 min |
| Step 6 | 68% C for 7 min |
| Step 7 | Repeat step 4–6 for 15 additional cycles |
| Step 8 | 94% C for 15 sec |
| Step 9 | 65% C for 1 min |
| Step 10 | 68% C for 7:15 min |
| Step 11 | Repeat step 8–10 for 12 cycles |
| Step 12 | 72% C for 8 min |
| Step 13 | 4% C (and holding) |

A 5-0 microliter aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 microliter of ligation buffer, 1 microliter T4-DNA ligase (15 units) and 1 microliter T4 polynucleotide kinase are added, and the mixture is incubated at room temperature for 2–3 hours or overnight at 16° C. Competent *E. coli* cells (in 40 & 1 of appropriate media) are transformed with 3 microliter of ligation mixture and cultured in 80 & 1 of SOC medium (Sambrook Jet al, supra). After incubation for one hour at 37° C., the whole transformation mixture is plated on Luria Bertani (LB)-agar (Sambrook Jet al, supra) containing 2×Carb. The following day, several colonies are randomly picked from each plate and cultured in 150 microliter of liquid LB/2×Carb medium placed in an individual well of an appropriate, commercially-available, sterile 96-well microtiter plate. The following day, 5 microliter of each overnight culture is transferred into a non- sterile 96-well plate and after dilution 1:10 with water, 5 microliter of each sample is transferred into a PCR array.

For PCR amplification, 18 microliter of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94% C for 60 sec |
| Step 2 | 94% C for 20 sec |
| Step 3 | 55% C for 30 sec |
| Step 4 | 72% C for 90 sec |
| Step 5 | Repeat steps 2–4 for an additional 29 cycles |
| Step 6 | 72% C for 180 sec |
| Step 7 | 4% C (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$^{-32}$P] adenosine triphosphate (Amersham, Chicago, Ill.) and T4 polynucleotide kinase (DuPont NEN®, Boston, Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

The HPHKG encoding sequence, or any part thereof, is used to inhibit in vivo or in vitro expression of naturally occurring hphkg. Although use of antisense oligonucleotides, comprising about 20 base-pairs, is specifically described, essentially the same procedure is used with larger cDNA fragments. For example, an oligonucleotide based on the coding sequence of HPHKG-1 as shown in FIG. 1 is used to inhibit expression of naturally occurring HPHKG. The complementary oligonucleotide is designed from the most unique 5' sequence as shown in FIG. 1 and used to inhibit translation of an HPHKG encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIG. 1.

VIII Expression of HPHKG

Expression of the HPHKG is accomplished by subcloning the cDNAs into appropriate vectors and transfecting the vectors into host cells. In this case, the cloning vector, pSport, previously used for the generation of the cDNA library is used to express HPHKG in $E.$ $coli.$ Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HPHKG. The signal sequence directs the secretion of HPHKG into the bacterial growth media which can be used directly in the following assay for activity.

IX HPHKG Activity

HPHKG activity may be assessed by phosphorylation of phosphorylase b using gamma-labeled $^{32}$P-ATP and quantitation of the incorporated radioactivity using a gamma radioisotope counter (Huang et al (1995), supra). HPHKG is incubated with phosphorylase b, $^{32}$P-ATP, and a kinase buffer. The $^{32}$P incorporated into the phosphorylase b is separated from free $^{32}$P-ATP by electrophoresis or by precipitation of the 32P-labeled protein and the incorporated $^{32}$P is counted.

X Production of HPHKG Specific Antibodies

HPHKG substantially purified using PAGE electrophoresis (Sambrook, supra) is used to immunize rabbits and to produce antibodies using standard protocols. The amino acid sequence translated from HPHKG is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 4 and 5) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HPHKG Using Specific Antibodies

Naturally occurring or recombinant HPHKG is substantially purified by immunoaffinity chromatography using antibodies specific for HPHKG. An immunoaffinity column is constructed by covalently coupling HPHKG antibody to an activated chromatographic resin such as CnBr-activated Sepharose (Pharmacia Biotech). After the coupling, the resin is blocked and washed according to the manufacturer's instructions.

Media containing HPHKG is passed over the immunoaffinity column, and the column is washed under conditions that allow the preferential absorbance of HPHKG (eg, high ionic strength buffers in the presence of detergent). The column is eluted under conditions that disrupt antibody/HPHKG binding (eg, a buffer of pH 2–3 or a high concentration of a chaotrope such as urea or thiocyanate ion), and HPHKG is collected.

XII Identification of Molecules Which Interact with HPHKG

HPHKG, or biologically active fragments thereof, are labelled with $^{125}$I Bolton-Hunter reagent (Bolton AE and Hunter WM (1973) Biochem J 133:529). Candidate molecules previously arrayed in the wells of a 96 well plate are incubated with the labelled HPHKG, washed and any wells with labelled HPHKG complex are assayed. Data obtained using different concentrations of HPHKG are used to calculate values for the number, affinity, and association of HPHKG with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

We claim:

1. An isolated and purified human phosphorylase kinase gamma subunit polynucleotide sequence encoding the polypeptide of SEQ ID NO:1.

2. An isolated and purified polynucleotide sequence of claim 1 consisting of the sequence of SEQ ID NO:2.

3. A polynucleotide sequence which is complementary to the sequence of SEQ ID NO:2.

4. A recombinant expression vector comprising the polynucleotide sequence of claim 1.

5. A recombinant host cell comprising the expression vector of claim 4.

6. A method for producing a polypeptide comprising the amino acid sequence shown in SEQ ID NO:1, the method comprising the steps of:

a) culturing the host cell of claim 5 under conditions suitable for the expression of the polypeptide; and b) recovering the polypeptide from the host cell culture.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
  ( A ) LENGTH: 307 amino acids
  ( B ) TYPE: amino acid
  ( C ) STRANDEDNESS: single
  ( D ) TOPOLOGY: linear ( i i ) MOLECULE TYPE: peptide ( v i i ) IMMEDIATE SOURCE:
  ( A ) LIBRARY:
  ( B ) CLONE: Consensus ( x i ) SEQUENCE DESCRIPTION: SEQ ID NO:1:

```
Met Arg Lys Arg Arg Lys Gly Gln Asp Cys Arg Met Glu Ile Ile His
 1               5                  10                  15

Glu Ile Ala Val Leu Glu Leu Ala Gln Asp Asn Pro Trp Val Ile Asn
            20                  25                  30

Leu His Glu Val Tyr Glu Thr Ala Ser Glu Met Ile Leu Val Leu Glu
        35                  40                  45

Tyr Ala Ala Gly Gly Glu Ile Phe Asp Gln Cys Val Ala Asn Arg Glu
 50                  55                  60

Asp Ala Phe Lys Glu Lys Asp Val Gln Arg Leu Met Arg Gln Ile Leu
 65                  70                  75                  80

Glu Gly Val His Phe Leu His Thr Arg Asp Val Val His Leu Asp Leu
                85                  90                  95

Lys Pro Gln Asn Ile Leu Leu Thr Ser Glu Ser Pro Leu Gly Asp Ile
            100                 105                 110

Lys Ile Val Asp Phe Gly Leu Ser Arg Ile Leu Lys Asn Ser Glu Glu
        115                 120                 125

Leu Arg Glu Ile Met Gly Thr Pro Glu Tyr Val Ala Pro Glu Ile Leu
130                 135                 140

Ser Tyr Asp Pro Ile Ser Met Ala Thr Asp Met Trp Ser Ile Gly Val
145                 150                 155                 160

Leu Thr Tyr Val Met Leu Thr Gly Ile Ser Pro Phe Leu Gly Asn Asp
                165                 170                 175

Lys Gln Glu Thr Phe Leu Asn Ile Ser Gln Met Asn Leu Ser Tyr Ser
            180                 185                 190

Glu Glu Glu Phe Asp Val Leu Ser Glu Ser Ala Val Asp Phe Ile Arg
        195                 200                 205

Thr Leu Leu Val Lys Lys Pro Glu Asp Arg Ala Thr Ala Glu Glu Cys
210                 215                 220

Leu Lys His Pro Trp Leu Thr Gln Ser Ser Ile Gln Glu Pro Ser Phe
225                 230                 235                 240

Arg Met Glu Lys Ala Leu Glu Glu Ala Asn Ala Leu Gln Glu Gly His
                245                 250                 255

Ser Val Pro Glu Ile Asn Ser Asp Thr Asp Lys Ser Glu Thr Glu Glu
            260                 265                 270

Ser Ile Val Thr Glu Glu Leu Ile Val Val Thr Ser Tyr Thr Leu Gly
        275                 280                 285

Gln Cys Arg Gln Ser Glu Lys Glu Lys Met Glu Gln Lys Ala Ile Ser
290                 295                 300

Gln Thr Ile
305
```

( 2 ) INFORMATION FOR SEQ ID NO:2:

( i ) SEQUENCE CHARACTERISTICS:
    ( A ) LENGTH: 1417 base pairs

-continued (B) TYPE: nucleic acid
(C) STRANDEDNESS: single
(D) TOPOLOGY: linear (ii) MOLECULE TYPE: cDNA (vii) IMMEDIATE SOURCE:
(A) LIBRARY:
(B) CLONE: Consensus (xi) SEQUENCE DESCRIPTION: SEQ ID NO:2:

| | | | | | |
|---|---|---|---|---|---|
| CGGGAGCTGG | GCAGGGGGAA | ATTTGCAGTG | GCTGACAAAA | TGTATAAAGA | AAGATTCTGG | 60 |
| GAAAGAATTT | GCTGCAAAGT | TCATGAGAAA | AAGAAGAAAA | GGCCAAGATT | GTCGGATGGA | 120 |
| AATAATTCAT | GAGATTGCTG | TACTTGAACT | AGCACAAGAC | AATCCTTGGG | TCATTAATTT | 180 |
| ACATGAAGTT | TATGAGACTG | CATCAGAAAT | GATCTTAGTT | CTGGAATATG | CTGCTGGGGG | 240 |
| TGAAATCTTT | GACCAGTGTG | TTGCAAACAG | AGAAGATGCC | TTTAAAGAAA | AAGATGTTCA | 300 |
| AAGACTTATG | CGACAGATTT | TAGAAGGTGT | TCACTTTTTA | CACACTCGTG | ATGTAGTTCA | 360 |
| TCTTGATTTG | AAGCCTCAGA | ATATTCTGTT | GACAAGTGAA | TCTCCATTGG | GTGACATTAA | 420 |
| GATTGTTGAT | TTTGGCCTYT | CAAGAATATT | GAAGAACAGT | GAAGAGCTCC | GAGAAATTAT | 480 |
| GGGTACCCCT | GAATATGTGG | CTCCTGAAAT | TCTTAGTTAT | GATCCTATAA | GCATGGCAAC | 540 |
| AGATATGTGG | AGCATTGGAG | TGTTAACATA | TGTCATGCTT | ACAGGAATAT | CACCTTTCTT | 600 |
| AGGCAATGAT | AAACAAGAAA | CATTCTTAAA | CATCTCACAG | ATGAATTTAA | GTTATTCTGA | 660 |
| GGAAGAATTT | GATGTTTTGT | CTGAGTCGGC | TGTTGATTTC | ATCAGGACAC | TTTTAGTTAA | 720 |
| GAAACCTGAA | GATCGAGCCA | CTGCTGAAGA | ATGTCTAAAG | CACCCCTGGT | TGACACAGAG | 780 |
| CAGTATTCAA | GAGCCTTCTT | TCAGGATGGA | AAAGGCACTA | GAAGAAGCAA | ATGCCCTCCA | 840 |
| AGAAGGTCAT | TCTGTGCCTG | AAATTAATTC | GGATACCGAC | AAATCAGAAA | CCGAGGAATC | 900 |
| CATTGTAACC | GAAGAGTTAA | TTGTAGTTAC | TTCATATACT | CTAGGACAAT | GCAGACAGTC | 960 |
| TGAAAAAGAG | AAAATGGAGC | AAAAGGCCAT | TTCCCAAACG | ATTTAAATTT | GAGGAACCTT | 1020 |
| TGCCTACAAG | AAATTCCAGG | AGAATTTATC | TACTGAGCAA | TATTTCCCTT | TAGAACTTCA | 1080 |
| AGATTTCTAC | ACTGAAAATG | TTAATATTAT | TTATGGACCT | CTGGCCAAAT | GGTACATGTA | 1140 |
| CTGGAAGTGG | ATAACCAGTA | TCACTTACAC | AAACAAAAAT | AACTTTGTCA | AATTTGTGGA | 1200 |
| GTTAGGTGGA | AGCCAGATTT | AAAAGTTGC | CAACCAGGAT | ATTTAACAGG | TACAGTTACC | 1260 |
| CGTTTCAATG | TTATTTTTAA | GAAGGGAGAT | GTTGGCACCT | TTGAATTCTA | CATCCTGTTT | 1320 |
| CTCCAGAATG | AGAATTTGTG | TACAAAGATA | TTTGTATTCA | CTTTCTTTAA | AAAATCCAAG | 1380 |
| TAAAAGTGCC | AAAACTACAA | AAAAAAAAA | AAAAAA | | | 1417 |

(2) INFORMATION FOR SEQ ID NO:3:

(i) SEQUENCE CHARACTERISTICS:
(A) LENGTH: 387 amino acids
(B) TYPE: amino acid
(C) STRANDEDNESS: single
(D) TOPOLOGY: linear (ii) MOLECULE TYPE: peptide (vii) IMMEDIATE SOURCE:
(A) LIBRARY: GenBank
(B) CLONE: 1147567

(xi) SEQUENCE DESCRIPTION: SEQ ID NO:3:

| Met | Thr | Arg | Asp | Glu | Ala | Leu | Pro | Asp | Ser | His | Ser | Ala | Gln | Asp | Phe |
|---|---|---|---|---|---|---|---|---|---|---|---|---|---|---|---|
| 1 | | | | 5 | | | | | 10 | | | | | 15 | |

-continued

```
Tyr Glu Asn Tyr Glu Pro Lys Glu Ile Leu Gly Arg Gly Val Ser Ser
         20              25              30

Val Val Arg Arg Cys Ile His Lys Pro Thr Ser Gln Glu Tyr Ala Val
         35              40              45

Lys Val Ile Asp Val Thr Gly Gly Ser Phe Ser Pro Glu Glu Val
     50              55              60

Arg Glu Leu Arg Glu Ala Thr Leu Lys Glu Val Asp Ile Leu Arg Lys
 65              70              75              80

Val Ser Gly His Pro Asn Ile Ile Gln Leu Lys Asp Thr Tyr Glu Thr
                 85              90              95

Asn Thr Phe Phe Phe Leu Val Phe Asp Leu Met Lys Arg Gly Glu Leu
             100             105             110

Phe Asp Tyr Leu Thr Glu Lys Val Thr Leu Ser Glu Lys Glu Thr Arg
         115             120             125

Lys Ile Met Arg Ala Leu Leu Glu Val Ile Cys Thr Leu His Lys Leu
     130             135             140

Asn Ile Val His Arg Asp Leu Lys Pro Glu Asn Ile Leu Leu Asp Asp
 145             150             155             160

Asn Met Asn Ile Lys Leu Thr Asp Phe Gly Phe Ser Cys Gln Leu Glu
             165             170             175

Pro Gly Glu Arg Leu Arg Glu Val Cys Gly Thr Pro Ser Tyr Leu Ala
             180             185             190

Pro Glu Ile Ile Glu Cys Ser Met Asn Glu Asp His Pro Gly Tyr Gly
         195             200             205

Lys Glu Val Asp Met Trp Ser Thr Gly Val Ile Met Tyr Thr Leu Leu
     210             215             220

Ala Gly Ser Pro Pro Phe Trp His Arg Lys Gln Met Leu Met Leu Arg
 225             230             235             240

Met Ile Met Ser Gly Asn Tyr Gln Phe Gly Ser Pro Glu Trp Asp Asp
             245             250             255

Tyr Ser Asp Thr Val Lys Asp Leu Val Ser Arg Phe Leu Val Val Gln
         260             265             270

Pro Gln Asn Arg Tyr Thr Ala Glu Glu Ala Leu Ala His Pro Phe Phe
     275             280             285

Gln Gln Tyr Leu Val Glu Glu Val Arg His Phe Ser Pro Arg Gly Lys
 290             295             300

Phe Lys Val Ile Ala Leu Thr Val Leu Ala Ser Val Arg Ile Tyr Tyr
 305             310             315             320

Gln Tyr Arg Arg Val Lys Pro Val Thr Arg Glu Ile Val Ile Arg Asp
             325             330             335

Pro Tyr Ala Leu Arg Pro Leu Arg Arg Leu Ile Asp Ala Tyr Ala Phe
             340             345             350

Arg Ile Tyr Gly His Trp Val Lys Lys Gly Gln Gln Gln Asn Arg Ala
         355             360             365

Ala Leu Phe Glu Asn Thr Pro Lys Ala Val Leu Leu Ser Leu Ala Glu
     370             375             380

Glu Asp Tyr
 385
```

( 2 ) INFORMATION FOR SEQ ID NO:4:

( i ) SEQUENCE CHARACTERISTICS:
( A ) LENGTH: 388 amino acids
( B ) TYPE: amino acid
( C ) STRANDEDNESS: single
( D ) TOPOLOGY: linear (ii) MOLECULE TYPE: peptide (vii) IMMEDIATE SOURCE:
(A) LIBRARY: GenBank
(B) CLONE: 200341

(xi) SEQUENCE DESCRIPTION: SEQ ID NO:4:

| Met | Thr | Arg | Asp | Asp | Ala | Leu | Pro | Asp | Ser | His | Ser | Ala | Gln | Thr | Phe |
|---|---|---|---|---|---|---|---|---|---|---|---|---|---|---|---|
| 1 | | | | 5 | | | | | 10 | | | | | 15 | |
| Tyr | Glu | Asn | Tyr | Glu | Pro | Lys | Glu | Ile | Leu | Gly | Arg | Gly | Val | Ser | Ser |
| | | | 20 | | | | | 25 | | | | | 30 | | |
| Val | Val | Arg | Arg | Cys | Ile | His | Lys | Pro | Thr | Cys | Gln | Glu | Tyr | Ala | Val |
| | | | 35 | | | | 40 | | | | | 45 | | | |
| Lys | Ile | Ile | Asp | Ile | Thr | Gly | Gly | Ser | Phe | Ser | Ser | Glu | Glu | Val | |
| | 50 | | | | | 55 | | | | | 60 | | | | |
| Gln | Glu | Leu | Arg | Glu | Ala | Thr | Leu | Lys | Glu | Val | Asp | Ile | Leu | Gln | Lys |
| 65 | | | | | 70 | | | | | 75 | | | | | 80 |
| Val | Ser | Gly | His | Pro | Asn | Ile | Ile | Gln | Leu | Lys | Asp | Thr | Tyr | Glu | Thr |
| | | | | 85 | | | | | 90 | | | | | 95 | |
| Asn | Thr | Phe | Phe | Phe | Leu | Val | Phe | Asp | Leu | Met | Lys | Arg | Gly | Glu | Leu |
| | | | 100 | | | | | 105 | | | | | 110 | | |
| Phe | Asp | Tyr | Leu | Thr | Glu | Lys | Val | Thr | Leu | Thr | Glu | Lys | Glu | Thr | Arg |
| | | 115 | | | | | 120 | | | | | 125 | | | |
| Lys | Ile | Met | Arg | Ala | Leu | Leu | Glu | Val | Ile | Cys | Thr | Leu | His | Lys | Leu |
| | 130 | | | | | 135 | | | | | 140 | | | | |
| Asn | Ile | Val | His | Arg | Asp | Leu | Lys | Pro | Glu | Asn | Ile | Leu | Leu | Asp | Asp |
| 145 | | | | | 150 | | | | | 155 | | | | | 160 |
| Asn | Met | Asn | Ile | Lys | Leu | Thr | Asp | Phe | Gly | Phe | Ser | Cys | Gln | Leu | Gln |
| | | | | 165 | | | | | 170 | | | | | 175 | |
| Pro | Gly | Glu | Lys | Leu | Arg | Glu | Val | Cys | Gly | Thr | Pro | Ser | Tyr | Leu | Ala |
| | | | 180 | | | | | 185 | | | | | 190 | | |
| Pro | Glu | Ile | Ile | Gln | Cys | Ser | Met | Asp | Asp | Gly | His | Pro | Gly | Tyr | Gly |
| | | 195 | | | | | 200 | | | | | 205 | | | |
| Lys | Glu | Val | Asp | Met | Trp | Ser | Thr | Gly | Val | Ile | Met | Tyr | Thr | Leu | Leu |
| | 210 | | | | | 215 | | | | | 220 | | | | |
| Ala | Gly | Ser | Pro | Pro | Phe | Trp | His | Arg | Lys | Gln | Met | Leu | Met | Leu | Arg |
| 225 | | | | | 230 | | | | | 235 | | | | | 240 |
| Met | Ile | Met | Asp | Gly | Lys | Tyr | Gln | Phe | Gly | Ser | Pro | Glu | Trp | Asp | Asp |
| | | | | 245 | | | | | 250 | | | | | 255 | |
| Tyr | Ser | Asp | Thr | Val | Lys | Asp | Leu | Val | Ser | Arg | Phe | Leu | Val | Val | Gln |
| | | | 260 | | | | | 265 | | | | | 270 | | |
| Pro | Gln | Asp | Arg | Cys | Ser | Ala | Glu | Glu | Ala | Leu | Ala | His | Pro | Phe | Phe |
| | | 275 | | | | | 280 | | | | | 285 | | | |
| Gln | Glu | Tyr | Val | Val | Glu | Glu | Val | Arg | His | Phe | Ser | Pro | Arg | Gly | Lys |
| | 290 | | | | | 295 | | | | | 300 | | | | |
| Phe | Lys | Val | Ile | Cys | Leu | Thr | Val | Val | Ala | Ser | Val | Lys | Ile | Tyr | Tyr |
| 305 | | | | | 310 | | | | | 315 | | | | | 320 |
| Gln | Tyr | Arg | Arg | Val | Lys | Pro | Val | Thr | Arg | Glu | Ile | Val | Ile | Arg | Asp |
| | | | 325 | | | | | 330 | | | | | 335 | | |
| Pro | Tyr | Ala | Leu | Arg | Pro | Leu | Arg | Arg | Leu | Ile | Asp | Ala | Tyr | Ala | Phe |
| | | | 340 | | | | | 345 | | | | | 350 | | |
| Arg | Ile | Tyr | Gly | His | Trp | Val | Lys | Lys | Gly | Gln | Gln | Asn | Arg | Ala | |
| | | | 355 | | | | 360 | | | | | 365 | | | |
| Ala | Leu | Phe | Glu | Asn | Thr | Pro | Lys | Ala | Val | Leu | Leu | Ser | Leu | Ala | Glu |
| 370 | | | | | 375 | | | | | 380 | | | | | |

Glu Glu Asp Phe
385

( 2 ) INFORMATION FOR SEQ ID NO:5:

( i ) SEQUENCE CHARACTERISTICS:
        ( A ) LENGTH: 388 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 569727

( x i ) SEQUENCE DESCRIPTION: SEQ ID NO:5:

```
Met Thr Arg Asp Glu Ala Leu Pro Asp Ser His Ser Ala Gln Asn Phe
 1               5                  10                  15

Tyr Glu Asn Tyr Glu Pro Lys Glu Ile Leu Gly Arg Gly Val Ser Ser
                20                  25                  30

Val Val Arg Arg Cys Ile His Lys Pro Thr Cys Gln Glu Tyr Ala Val
            35                  40                  45

Lys Ile Ile Asp Ile Thr Gly Gly Gly Ser Phe Ser Ser Glu Glu Val
        50                  55                  60

Gln Glu Leu Arg Glu Ala Thr Leu Lys Glu Val Asp Ile Leu Gln Lys
65                  70                  75                  80

Val Ser Gly His Pro Asn Ile Ile Gln Leu Lys Asp Thr Tyr Glu Thr
                85                  90                  95

Asn Thr Phe Phe Phe Leu Val Phe Asp Leu Met Lys Arg Gly Glu Leu
                100                 105                 110

Phe Asp Tyr Leu Thr Glu Lys Val Thr Leu Thr Glu Lys Glu Thr Arg
            115                 120                 125

Lys Ile Met Arg Ala Leu Leu Glu Val Val Cys Thr Leu His Lys Leu
        130                 135                 140

Asn Ile Val His Arg Asp Leu Lys Pro Glu Asn Ile Leu Leu Asp Asp
145                 150                 155                 160

Asn Met Asn Ile Lys Leu Thr Asp Phe Gly Phe Ser Cys Gln Leu Gln
                165                 170                 175

Pro Gly Glu Lys Leu Arg Glu Val Cys Gly Thr Pro Ser Tyr Leu Ala
                180                 185                 190

Pro Glu Ile Ile Gln Cys Ser Met Asp Glu Gly His Pro Gly Tyr Gly
            195                 200                 205

Lys Glu Val Asp Met Trp Ser Thr Gly Val Ile Met Tyr Thr Leu Leu
    210                 215                 220

Ala Gly Ser Pro Pro Phe Trp His Arg Lys Gln Met Leu Met Leu Arg
225                 230                 235                 240

Met Ile Met Asp Gly Lys Tyr Gln Phe Gly Ser Pro Glu Trp Asp Asp
                245                 250                 255

Tyr Ser Asp Thr Val Lys Asp Leu Val Ser Arg Phe Leu Val Val Gln
            260                 265                 270

Pro Gln Asp Arg Cys Ser Ala Glu Glu Ala Leu Ala His Pro Phe Phe
        275                 280                 285

Gln Glu Tyr Val Val Glu Glu Val Arg His Phe Ser Pro Arg Gly Lys
    290                 295                 300

Phe Lys Val Ile Cys Leu Thr Val Leu Ala Ser Val Arg Ile Tyr Tyr
305                 310                 315                 320
```

-continued

| Gln | Tyr | Arg | Arg | Val 325 | Lys | Pro | Val | Thr | Arg 330 | Glu | Ile | Val | Ile | Arg 335 | Asp |
| --- | --- | --- | --- | --- | --- | --- | --- | --- | --- | --- | --- | --- | --- | --- | --- |
| Pro | Tyr | Ala | Leu 340 | Arg | Pro | Leu | Arg | Arg 345 | Leu | Ile | Asp | Ala | Tyr 350 | Ala | Phe |
| Arg | Ile | Tyr 355 | Gly | His | Trp | Val | Lys 360 | Lys | Gly | Gln | Gln | Gln 365 | Asn | Arg | Ala |
| Ala | Leu 370 | Phe | Glu | Asn | Thr | Pro 375 | Lys | Ala | Val | Leu | Leu 380 | Ser | Leu | Ala | Glu |
| Glu 385 | Glu | Asp | Phe | | | | | | | | | | | | |